(12) United States Patent  
Fuchs

(10) Patent No.: US 7,840,039 B2
(45) Date of Patent: Nov. 23, 2010

(54) METHOD AND SYSTEM FOR DISPLAYING CONFIDENCE INTERVALS FOR SOURCE RECONSTRUCTION

(75) Inventor: Manfred Fuchs, Hamburg (DE)

(73) Assignee: Compumedics Limited, Abbotsford (AU)

( * ) Notice: Subject to any disclaimer, the term of this patent is extended or adjusted under 35 U.S.C. 154(b) by 891 days.

(21) Appl. No.: 10/520,046

(22) PCT Filed: Jul. 1, 2003

(86) PCT No.: PCT/US03/20915

§ 371 (c)(1),
(2), (4) Date: Dec. 27, 2005

(87) PCT Pub. No.: WO2004/006142

PCT Pub. Date: Jan. 15, 2004

(65) Prior Publication Data

US 2007/0165915 A1    Jul. 19, 2007

(51) Int. Cl.
*G06K 9/00* (2006.01)
(52) U.S. Cl. .................................... 382/128; 382/154
(58) Field of Classification Search ......... 382/128–132; 607/55, 407; 324/301, 302, 200–263; 600/407–409, 600/383, 386, 405, 301, 544, 513; 128/925
See application file for complete search history.

(56) References Cited

U.S. PATENT DOCUMENTS

| | | | | |
|---|---|---|---|---|
| 5,331,970 | A * | 7/1994 | Gevins et al. | 600/544 |
| 5,417,211 | A * | 5/1995 | Abraham-Fuchs et al. | 600/409 |
| 5,776,063 | A * | 7/1998 | Dittrich et al. | 600/408 |
| 6,073,040 | A * | 6/2000 | Kiyuna | 600/409 |
| 6,132,381 | A * | 10/2000 | Forbes et al. | 600/483 |
| 6,856,830 | B2 * | 2/2005 | He | 600/513 |
| 6,957,172 | B2 * | 10/2005 | Wegerich | 702/189 |

OTHER PUBLICATIONS

Braun et al, "Confidence anterval of SingUe Dipole Locations Based on EEG Data", Brain Topography, vol. 10, No. 1,1997.*
Yamazki et al, "The accuracy of localizing equivalent dipoles and thespatio-temporal correlations of background EEG", Biomedical Engineering, IEEE Transactions, Sep 1998, vol. 45, Issue: 9, On pp. 1114-1121.*
Fuchs M, Kullmann WH, DOSSK0I. Functional imaging of neuronal brain activities: overlay of distributed neuromagnetic current density images and morphological MR images. Eur Radio] 1933;3:41-48.*
Braun C et al: "Confidence interval of single dipole locations based on EEG data." Brain Topography. United States 1997 Fall, vol. 10, No. 1, Oct. 1997, pp. 31-99, XP009028341 ISSN: 0896-0267 in particular sections Introductions, Methods Head model, Linearization . . . , Iterative confidence interval . . . the whole document.

(Continued)

*Primary Examiner*—Anand Bhatnagar
*Assistant Examiner*—Andrae S Allison
(74) *Attorney, Agent, or Firm*—Briggs and Morgan, P.A.

(57) ABSTRACT

The present invention involves the creation of an appropriate model and the use of that model to generate a best fit dipole represented by a vector (x, y, z). Once the best fit dipole is generated, a best fit field distribution and a field distribution of a modified dipole is created. Using a difference between the field distributions, a Singular Value Decomposition is used to compute the main axes of the confidence ellipsoids.

18 Claims, 5 Drawing Sheets

OTHER PUBLICATIONS

Yamazyki T et al: "The Accuracy of Localizing Equivalent Dipoles and the Spatio—Temporal Correlations of Background EEG" IEEE Transactions on Biomedical Engineering, IEEE Inc, New York, US, vol. 45, No. 9, Sep. 1, 1998, pp. 1114-1121, XP000784379 ISSN: 0018-9294 in particular figure 2 the whole document.

Fuchs M et al: "Improving source reconstructions by combining bioelectric and biomagnetic data" Electroencephalography and Clinical Neurophysiology, Aug. 1998, Elsevier, Ireland, vol. 107, No. 2, pp. 93-111, XP002274982 ISSN: 0013-4694 in particular sections 2.1, 2.2, 2.5 the whole document.

Yamazaki T et al: "Confidence limits for the parameter estimation in the dipole localization method on the basis of spatial correlation of background EEG." Brain Topography. United States 1992 Winter, vol. 5, No. 2, Jan. 1992 pp. 195-198, XP009028340 ISSN: 0896-0267 the whole document.

Fuchs, et al., "Coordinate System Matching for Neuromagnetic and Morphological Reconstruction Overlay", *IEEE Transactions on Biomedical Engineering*, vol. 42, No. 4 Apr. 1995, 416-420.

Fuchs, M. et al., "Functional imaging of neuronal brain activities: overlay of distributed neuromagnetic current density images and morphological MR images", *Eur. Radiol. 3* 1993, 41-43.

Sarvas, "Basic mathematical and electromagnetic concepts of the biomagnetic inverse problem", *Phys. Med. Biol.*, vol. 32, No. 1 1987, 11-22.

\* cited by examiner

METHOD AND SYSTEM FOR DISPLAYING CONFIDENCE INTERVALS FOR SOURCE RECONSTRUCTION

FIELD OF THE INVENTION

Generally, the invention relates to the field of source imaging. More specifically, the invention relates to the calculation and display of a confidence interval for a dipole fit in a source reconstruction.

BACKGROUND OF THE INVENTION

Physicians and researchers often need to identify patches of electrically active cortical or myocardial tissue in order to identify a source of illness or to map brain activity. While known monitoring equipment are capable of determining that electrical or magnetic activity has occurred, the determination of a source of that activity must often be calculated or estimated. The process of calculating or estimating the source of electromagnetic activity in tissue is generally referred to as source reconstruction.

There are a number of different methods known in the art for performing source reconstruction. Many of these methods involve creating a model which attempts to determine the source of activity through the use of mathematical formulas which describe electromagnetic field distributions. These formulas typically depend on the position and orientation of the source, the position and orientation of the sensors which pick up the electromagnetic signals, and the geometry and conductivity properties of the volume conductor (head or chest) tissue.

One known method of source reconstruction involves the determination of equivalent current dipoles. This method makes the basic assumption that the source of electromagnetic activity is focal and small in number. However, measured data exhibits a limited Signal-to-Noise Ratio (SNR) due to background activity, environmental and amplifier noise. The noise distribution of the data leads to scattered dipole positions in the source space around the most probable source position. As such, the reconstructed dipoles only represent the most probable source positions.

There is a need for an apparatus and a method to determine and to display an area surrounding the reconstructed dipoles which represent a most probable solution to the source reconstruction model given the noise level in the data. This area is generally known as a confidence interval and it represents a probability distribution which corresponds to the noise level.

SUMMARY OF THE INVENTION

The present invention is a method and an apparatus for displaying the confidence interval of a source reconstruction result. In one embodiment, an Equivalent Current Dipole (ECD) model is used to perform the source reconstruction. The ECD model defines a current dipole in terms of its location, strength and orientation, along with an estimate of its reliability (confidence volume). When using the ECD model, one of the vectors generated represents the source dipole location (the more important one since it represents the result of the non-linear least squares fit procedure). Another vector that is reconstructed represents the dipole orientation (solution of a linear inverse problem), so both result vectors should be distinguished. In order to compute the best fit field, both result vectors are needed.

Once the best fit dipole is generated, it is used to create a best fit field distribution. The best fit dipole position is also modified by a small amount (generally less than 1 mm) and a field distribution of the modified dipole is created. A difference between the best fit field distribution generated and the modified field distribution is computed and a Singular Value Decomposition is used to determine the main axes of confidence ellipsoid. An analysis of the signal noise is performed, and an estimate of the SNR is generated. A confidence interval is calculated from the estimated noise level and the difference of field strength. The confidence interval is then overlaid onto an anatomical image of the source tissue.

BRIEF DESCRIPTION OF THE DRAWINGS AND FIGURES

For purposes of facilitating and understanding the subject matter sought to be protected, there is illustrated in the accompanying drawings an embodiment thereof. From an inspection of the drawings, when considered in connection with the following description, the subject matter sought to be protected, its construction and operation, and many of its advantages should be readily understood and appreciated.

DETAILED DESCRIPTION OF THE PREFERRED EMBODIMENTS

A. General Overview

Figure 1:
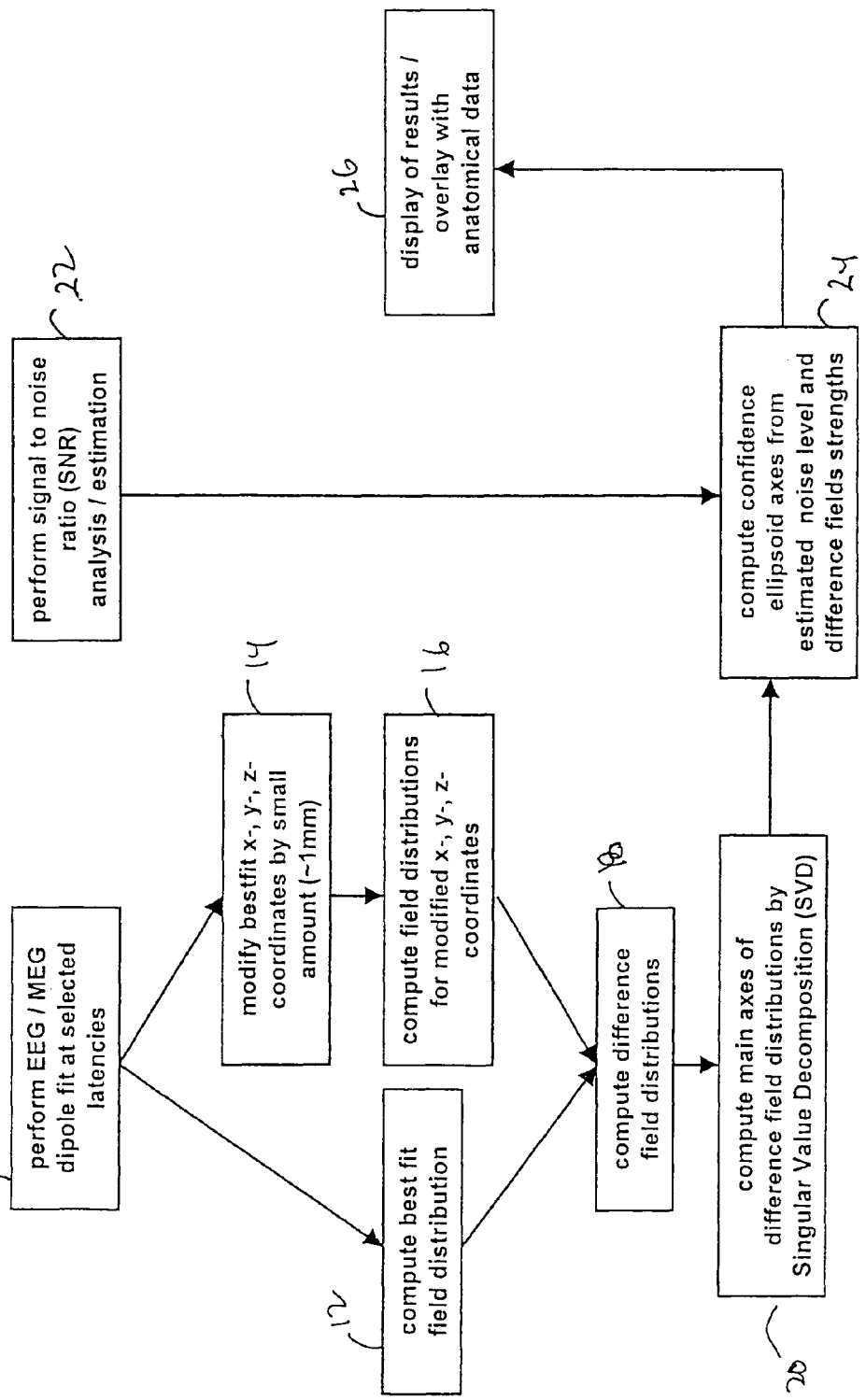
FIG. 1 is a flow chart of the present invention, the subject method of determining and displaying a confidence interval.

FIG. 1 is a flowchart providing a general overview of the present invention. Box 10 represents the generation of a dipole fit at selected latencies. This step involves the creation of an appropriate model and the use of that model to generate a best fit dipole represented by a vector (x, y, z). Once the best fit dipole is generated, the vector is used to create a best fit field distribution as shown in box 12. The best fit dipole is also modified by a small amount (generally less than 1 mm) as shown in box 14 and a field distribution of the modified dipole is created box 16.

A difference between the field distribution generated in box 12 and the modified field distribution of box 16 is computed (box 18). A Singular Value Decomposition is used to compute the main axes of the confidence ellipsoids (box 20).

An analysis of the signal noise is performed, and an estimate of the SNR is generated (box 22). A confidence ellipsoid is calculated (box 24) from the estimated noise level of box 22 and the difference of field strength from box 20. The confidence interval is then overlaid onto an anatomical image of the source tissue (box 26).

B. Operation

Reference points are determined with using a Cartesian coordinate system anchored on (at least) three fiducial points on the subject's head. In one embodiment, the fiducial points include two external ear canal points and the nasion. The two ear canal points define the y-axis. The line perpendicular to the y-axis and passing through the nasion defines the x-axis, and the line perpendicular to the x-y plane passing at the intersection of the x-y axis defines the z axis.

Once the frame of reference has been established, appropriate models have to be used to reconstruct the source of the measured electromagnetic data. Neural activity can often be represented as a primary source with a specific current density in a closed volume. The current density is comprised of primary (intracellular) and secondary (extracellular) components.

Localizing the primary current sources is known as solving the inverse problem. However, there is typically no unique solution to the inverse problem because there may be an infinite number of current distributions which could be used to explain the externally measured magnetic field or electrical potential. As such, it is necessary to make assumptions regarding the location or the geometry of the source.

Given a particular data set, an appropriate model is selected based on a particular model criterion. There are many model criterion that are known in the art. These formulas depend on the number, position and orientation of the current source, the position (and orientation in the magnetic case) of the sensors, and the geometry and conductivity properties of the head or heart tissue. For the purposes of explanation only, the embodiment of the present invention is described as using an ECD or elementary dipole model. The ECD model defines the current dipole in terms of its location, strength and orientation, along with an estimate of its reliability (confidence volume). One skilled in the art can readily appreciate that the present invention is easily adapted to support other known models.

In order to determine a best fit dipole, the ECD model is used because analytical or numerical expressions exist that describe their electromagnetic field distributions. For example, assuming an infinite homogeneous volume (used for the purpose of simplifying the mathematical explanation only, typically, spherical shell models, three or four shells representing skin, skull, and brain, or a Boundary/Finite Element Method model are used) conductor (conductivity $\sigma_o$, permeability $u_0$) a dipole at position $r$, current $j$, sensor at position $r$ will have the following electric potential $V_0$ and magnetic field $B_0$:

$$V_0 = \frac{1}{4\pi\sigma_0} j \frac{r - r_j}{|r - r_j|^3} \quad (1)$$

$$B_0 = \frac{\mu_0}{4\pi} j \times \frac{r - r_j}{|r - r_j|^3} \quad (2)$$

Due to the linearity in the dipole components of all volume conductor models the so-called lead-field fofprmulation provides a more compact notation comprising all sensor signals in column vectors:

$$\underline{V} = \underline{L}_V \underline{j} \text{ and } \underline{B} = \underline{L}_B \underline{j} \quad (3)$$

The lead-field matrices:

$$\underline{L}_V(3^* S_e) \text{ and } \underline{L}_B(3S_m)$$

contain all geometric information, such as dipole and sensor positions, and volume conductor properties, whereas the linear dipole components $\underline{j}$ and thereby the dipole orientations are separated.

In a spatio-temporal formulation, the vector $\underline{M}$ containing the measured data has to be extended to a matrix M, where each column vector represents one sample. Accordingly, the current component vector $\underline{j}$ has to be extended. For keeping the expressions better readable, the vector and matrix underlines are omitted in the following equations:

$$(\underline{j} \rightarrow j, \underline{L} \rightarrow L, \underline{M} \rightarrow M).$$

The best fit solution of the inverse problem is determined by minimizing the residual variance (squared deviation) between the measured data and the forward calculated fields using the Frobenius norm of a matrix A:

$$|A|^2 = \sum_{i=1}^{m} \sum_{k=1}^{n} a_{ik}^2 \quad (4)$$

$$\Delta^2 = |M - Lj|^2 \quad (5)$$

M is the spatio-temporal measured data matrix (s sensors * t samples), the lead-field matrix L (s·c current dipole components) comprises the dipole positions, the volume conductor characteristics, and the sensor geometry, and j contains the (c*t) temporal loadings or strengths of the (c=3·d dipoles) dipole components. The best fit currents ĵ, that minimize Eq. 5 in the overdetermined case (more knowns than unknowns: s>c) are given by [Lawson and Hanson, 1974; Ben-Israel and Greville, 1976]:

$$ĵ = (L^T L)^{-1} L^T M \quad (6)$$

The best fit dipole positions can then be found by nonlinear mininization algorithms (e.g. Nelder-Mead-simplex [Nelder and Mead, 1965]) (Box 10). For each dipole position or configuration the lead-field matrix L has to be set up and the best fit deviation (Eq. 5 with j=ĵ) is calculated by solving the linear problem for the dipole strengths (Eq. 6). The minimizer changes the nonlinear parameters (the dipole positions) and looks for the global minimum of the error hypersurface.

Once a best fit coordinate is found, a field distribution is calculated based on the best fit coordinate (Box 12). The best fit coordinates are also modified (in the order of 1 mm) (Box 14) and a field distribution is calculated based on the modified best fit coordinates (Box 16).

From Eq. 5 and 6, the best fit field distribution F is calculated as follows:

$$F = Lĵ = L(L^T L)^{-1} L^T M \quad (7)$$

The difference between best fit field distribution and the modified best fit coordinates is then calculated (Box 18). By modifying the best fit dipole coordinates $x_i = x, y, z$ by little increments $dx_i$, modified lead field matrices $L_1$, field distributions $F_1$, and the difference between the field distributions dF (normalized to the position changes) corresponding to these changes can be calculated as:

$$dF_i = (F_i - F)/dx_i \quad (8)$$

A main axes of the difference in field distributions is then computed by Singular Value Decomposition (SVD) (box 20). For each dipole position k three difference field vectors $dF_k$ (i=x, y, z) are obtained, that can be written as columns of a difference field matrix $dF_k$ (three columns, s rows). In a linear approximation, the main axes of the corresponding error ellipsoid can then be computed by a SVD of this matrix:

$$dF_k = U_k \Sigma_k V_k^T \quad (9)$$

The axis orientations are contained in rows of the three by three rotation matrix $V_k^T$ and the lengths of the axes $\Sigma_{ki}$ are obtained from the number of sensors s (due the normalization of the SVD), the mean noise level N, and the three singular values $\Sigma_{ki}$ $$l_{ki} = N\sqrt{s}/\Sigma_{ki} \quad (10)$$

In this linear approximation the lengths of the confidence ellipsoid axes are proportional to the noise level (Eq. 10) and thus the confidence volume $v_k$ proportional to the third power of the noise level N:

$$v_k = l_{kx} l_{ky} l_{kz} \cdot 4\pi/3 = 4\pi N^3 s^{3/2}/(3\Sigma_{kx}\Sigma_{ky}\Sigma_{kz}) \qquad (11)$$

Figure 2:
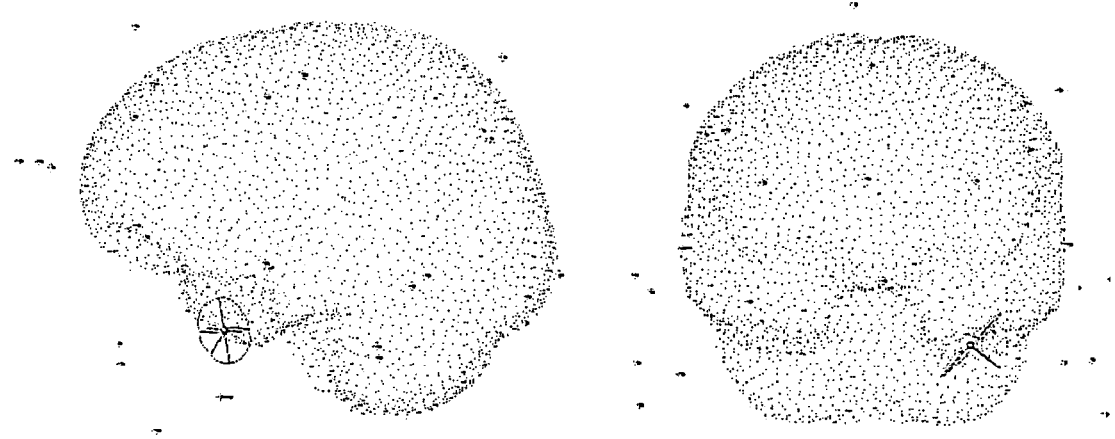
FIG. 2 is an illustration of a confidence interval overlaid onto a computer generated image of a cortex.

The confidence interval is then overlaid onto an anatomical map, using the coordinates of the best dipole fit and their circumference as shown in FIG. 2. In one embodiment, after registration of the two modalities (functional [EEG/MEG] and anatomical [MR/CT] coordinate system) which is done by matching at least three landmarks that can be identified in both modalitites, the confidence ellipsoids can be transformed into the anatomical coordinate system like the dipole positions and orientations using the same transformation algorithm (vector—matrix multiplication representing a rigid transformation [rotation and shift operation]).

Figure 3:
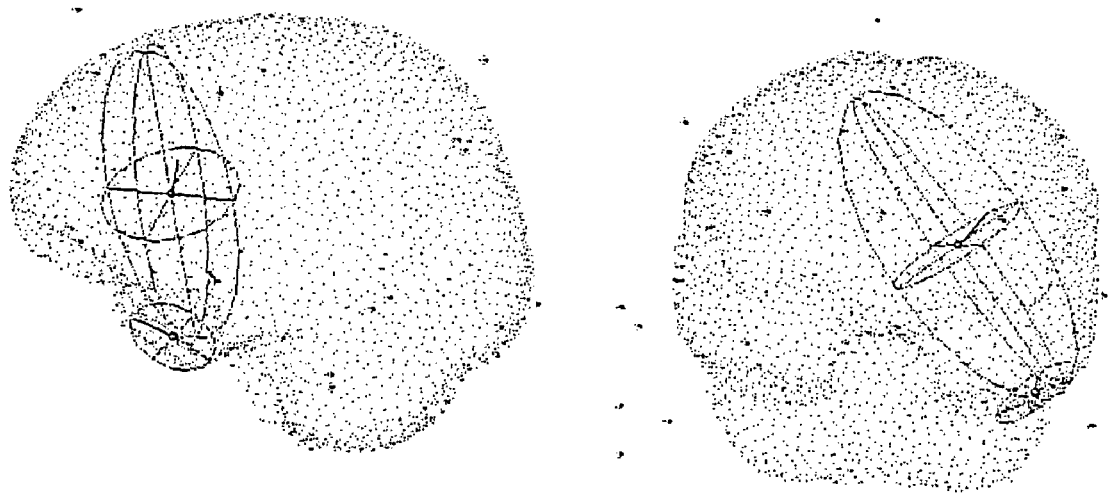
FIG. 3 is an illustration of the confidence ellipsoids as used to test a dipole model used.

FIG. 3 is an illustration for the ability of the confidence ellipsoids to be useful to test the dipole model used. In this case a two dipole model was applied to a data-set that could already be explained by a single dipole at the selected latency (FIG. 2). The meaningful dipole stays at the left temporal lobe, whereas the second dipole, that is not really needed to explain the measured data, can be everywhere within the left temporal frontal region. Without displaying the confidence ellipsoids, just two dipole symbols would be displayed, only the fit quality is slightly improved, due to larger degrees of freedom of the two dipole solution (six non-linear (position) parameters and six linear component parameters compared to three non-linear and three linear parameters in the one dipole case). The point cloud in both FIG. 2 and FIG. 3 is the same (points on the segmented cortical surface just for visualization purposes, this could also be a semi-transparent rendering of the cortical surface).

Figure 4:
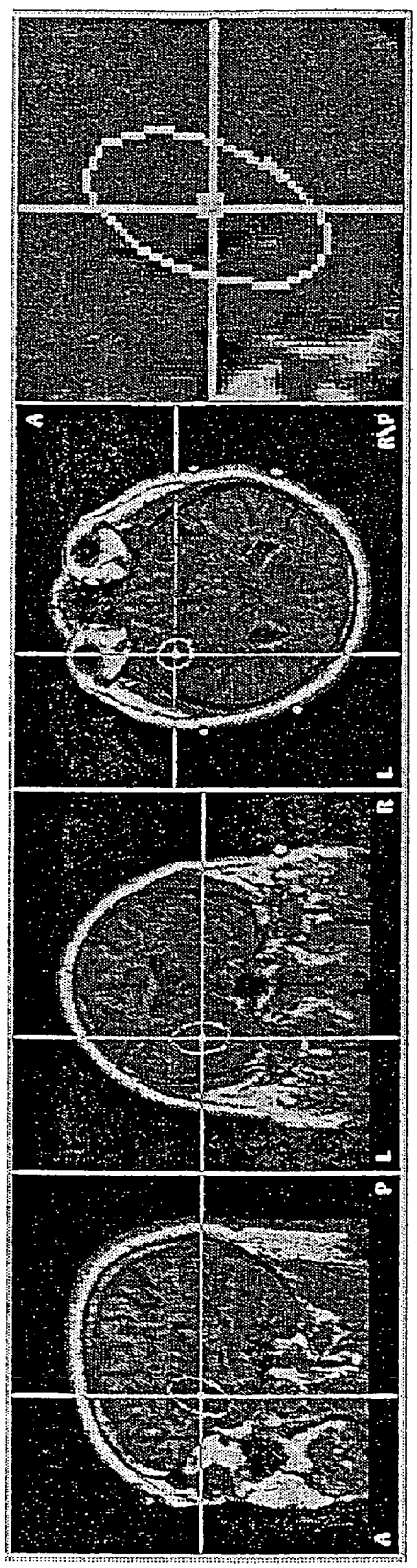
FIG. 4 is an illustration of a confidence interval overlaid onto an MRI.

As shown in FIG. 4, the confidence ellipsoid can also be overlaid over anatomical data in an orthogonal slice display. The ellipsoids are projected onto the corresponding planes of the anatomical data.

C. System Configuration

Figure 5:
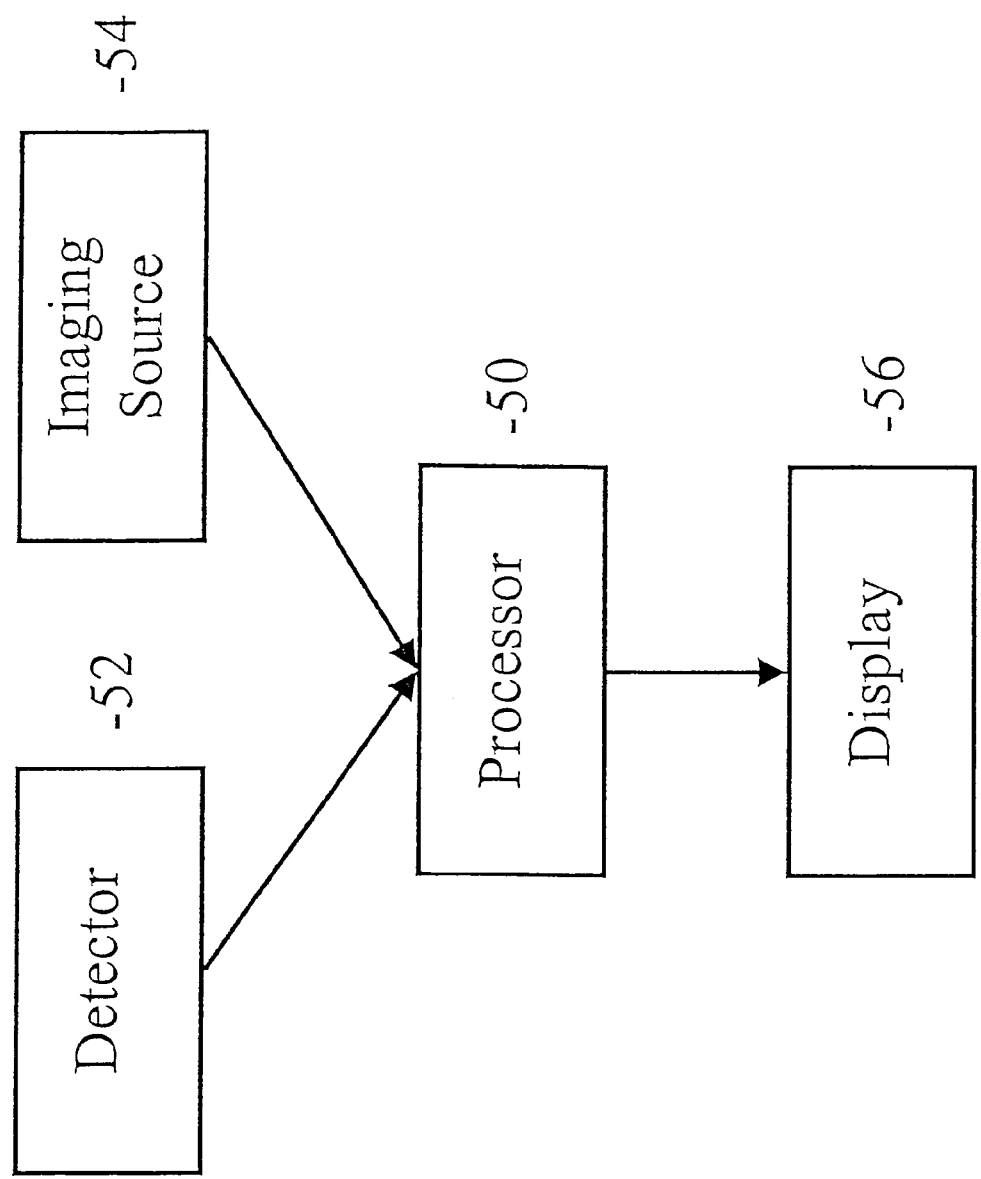
FIG. 5 is a schematic illustration of the present invention.

As shown in FIG. 5, in one embodiment, the present invention includes a processor 50 in communication with a detector 52, an imaging source 54, and a display 56. For the purposes of this disclosure, the term in communication shall include communication by hardwire means, by telecommunications means, or by the transfer of data using a memory device. The system components can be fully or partially integrated with each other, or they may be stand alone components.

The processor 50 can be a single or multiple computers, or can be any processor, integrator, or any hardwired circuit configured to perform the steps described in the subject invention.

The detector 52 can be any known physiological monitoring device or a combination thereof. Preferably, the detector is a combination of an Electroencephalogram (EEG) and a Magnetoencephalogram (MEG).

The imaging source 54 can be any known imaging device, but preferably, the imaging source is a Magnetic Resonance Imaging Unit (MRI) or a Computerized Tomography Unit (CT).

The display can be any that is known in the art, but preferably, the display is of a high resolution.

The matter set forth in the foregoing description and accompanying drawings is offered by way of illustration only and not as a limitation. While a particular embodiment has been shown and described, it will be obvious to those skilled in the art that changes and modifications may be made without departing from the broader aspects of applicant's contribution. The actual scope of the protection sought is intended to be defined in the following claims when viewed in their proper perspective based on the prior art.

What is claimed is:

1. A method comprising:
   modeling neural activity as single equivalent current dipoles (ECD's);
   calculating best fit dipole coordinates for each dipole;
   calculating a field distribution based on the best fit dipole coordinates;
   modifying the best fit dipole coordinates to create modified dipole coordinates;
   calculating a modified field distribution based on the modified dipole coordinates;
   computing a difference between the field distribution and the modified field distribution;
   computing a confidence interval for each dipole based on the difference between the field distribution and the modified field distribution; and
   displaying the confidence interval in an overlay on a three-dimensional image obtained through the use of either magnetic resonance imaging (MRI) or computerized tomography (CT).

2. The method of claim 1, wherein the step of computing a confidence interval includes computing an error ellipsoid using a Singular Value Decomposition.

3. The method of claim 1, wherein the step of modeling includes assuming the geometric and conductive properties of cardiac or cortical tissue.

4. The method of claim 1, wherein the step of computing a confidence interval includes the step of performing a signal to noise ratio analysis.

5. The method of claim 1, and further comprising defining a Cartesian coordinate system.

6. An apparatus comprising:
   a detector;
   a processor adapted to receive data from the detector, and using the processor to:
     calculate best fit dipole coordinates for each dipole;
     calculate a field distribution based on the best fit dipole coordinates;
     modify the best fit dipole coordinates to create modified dipole coordinates;
     calculate a modified field distribution based on the modified dipole coordinates;
     compute a difference between the field distribution and the modified field distribution; and compute a confidence interval for each dipole based on the difference between the field distribution and the modified field distribution;
   an imaging source in communication with the processor; and
   a display in communication with the processor and adapted to display the confidence interval in three dimensions relative to a three-dimensional anatomical image, wherein the three-dimensional anatomical image is obtained through the use of the imaging source.

7. The apparatus of claim 6, wherein the imaging source is an MRI unit.

8. The apparatus of claim 6, wherein the imaging source is a CT unit.

9. The apparatus of claim 6, wherein the detector comprises electroencephalogram sensors.

10. The apparatus of claim 6, wherein the detector comprises magnetoencephalogram sensors.

11. A method comprising:

measuring a plurality of electrical or magnetic signals;

calculating best fit dipole coordinates for each signal;

calculating a field distribution based on the best fit dipole coordinates;

modifying the best fit dipole coordinates to create modified dipole coordinates;

calculating a modified field distribution based on the modified dipole coordinates;

computing a difference between the field distribution and the modified field distribution;

computing a confidence interval for the best fit dipole coordinates for each signal based on the difference between the field distribution and the modified field distribution; and displaying the confidence interval on a three-dimensional anatomical map, wherein the confidence interval is displayed in its anatomical position in three dimensions.

12. The method of claim 11, wherein the step of computing a confidence interval includes computing confidence ellipsoid axes from an estimated noise level and different field strengths.

13. The method of claim 11, wherein the step of displaying includes the step of receiving a digital image.

14. The method of claim 11, wherein the step of computing a confidence interval includes the step of computing a confidence volume.

15. The apparatus of claim 7, wherein the detector comprises electroencephalogram sensors.

16. The apparatus of claim 8, wherein the detector comprises electroencephalogram sensors.

17. The method of claim 5, wherein the Cartesian coordinate system is anchored on at least three fiducial points on a patient's head.

18. The method of claim 11, further comprising defining a Cartesian coordinate system anchored on at least three fiducial points on a patient's head.

* * * * *

UNITED STATES PATENT AND TRADEMARK OFFICE
CERTIFICATE OF CORRECTION

PATENT NO. : 7,840,039 B2  
APPLICATION NO. : 10/520046  
DATED : November 23, 2010  
INVENTOR(S) : Fuchs Page 1 of 1

It is certified that error appears in the above-identified patent and that said Letters Patent is hereby corrected as shown below:

Title Page,
Item (60), Related U.S. Application Data is missing and should read:
-- Related U.S. Application Data
(60) Provisional application No. 60/393,908, filed on July 3, 2002. --

Signed and Sealed this
Thirteenth Day of September, 2011

David J. Kappos
*Director of the United States Patent and Trademark Office*